United States Patent [19]

Ranus, Jr. et al.

[11] 4,101,584
[45] Jul. 18, 1978

[54] BISBENZOIN ETHERS AND METHOD OF PRODUCING BENZOIN ETHERS

[75] Inventors: Walter J. Ranus, Jr., Midland Park; Lester Dennis McClure, Oakland, both of N.J.

[73] Assignee: Napp Chemicals Inc., Lodi, N.J.

[21] Appl. No.: 749,523

[22] Filed: Dec. 10, 1976

[51] Int. Cl.$^2$ .................. C07C 49/84; C08F 2/46; B29C 19/02
[52] U.S. Cl. .................. 260/590 D; 204/159.23; 156/272; 96/115; 96/35.1
[58] Field of Search .................. 260/590 D, 590 R

[56] References Cited
U.S. PATENT DOCUMENTS

| 3,689,565 | 9/1972 | Hoffmann et al. | 260/590 D |
| 3,728,377 | 4/1973 | Kelly et al. | 260/473 R |

FOREIGN PATENT DOCUMENTS 2,107,934  3/1970  Fed. Rep. of Germany ....... 260/590

OTHER PUBLICATIONS

Butenandt et al., Ber., vol. 72, pp. 182–187 (1939).

Primary Examiner—James O. Thomas, Jr.
Assistant Examiner—James H. Reamer
Attorney, Agent, or Firm—Steinberg & Blake

[57] ABSTRACT

New bisbenzoin ethers are produced. The method of producing the bisbenzoin ethers comprises the reaction of an alkyl glycol with benzoin utilizing phosphorous oxychloride as the catalyst with hydrogen chloride as acid reacting agent. The use of phosphorous oxychloride as catalyst with hydrogen chloride improves the production of benzoin ethers in general by the reaction of benzoin with the selected alcohol.

8 Claims, No Drawings

BISBENZOIN ETHERS AND METHOD OF PRODUCING BENZOIN ETHERS

BACKGROUND OF THE INVENTION

The invention generally relates to the production of benzoin ethers by reaction of benzoin with an alcohol utilizing phosphorous oxychloride as the catalyst for the reaction with hydrogen chloride as acid reacting agent.

The reaction of alkyl alcohols with benzoin to produce benzoin ethers is known utilizing various acid catalysts. However, even under carefully controlled operating conditions the yields did not exceed about 80%.

Furthermore, there is no indication of the known methods having been used to produce bisbenzoin ethers.

SUMMARY OF THE INVENTION

Generally speaking, in accordance with the present invention benzoin ethers are produced by reacting alcohols with benzoin utilizing phosphorous oxychloride as the acid catalyst along with hydrogen chloride. The method is applicable to the production of ethers of benzoin in general with the full series of alkyl alcohols.

The method also results in the production of bisbenzoin ethers by the reaction of benzoin with alkylene glycol.

It is accordingly a primary object of the present invention to provide a method of producing benzoin ethers in high yield and with a high degree of purity.

It is a further object of the present invention to provide a method of producing bisbenzoin ethers.

It is yet a further object of the present invention to provide for a simple method of directly producing benzoin ethers from benzoin and alcohols including glycols, by the reaction of the benzoin and the alcohol utilizing phosphorous oxychloride as catalyst, the reaction being carried out in the presence of an acid reacting agent, preferably hydrogen chloride gas.

With the above and other objects in view the present invention mainly comprises reacting an alcohol with benzoin in the presence of an acid reacting substance and phosphorous oxychloride as a catalyst.

The acid reacting substance is preferably hydrogen chloride gas and the reaction is preferably effected at the refluxing temperature of the reaction medium.

In order to avoid undesired side reactions, an excess of alcohol is utilized in the reaction, the excess alcohol acting as solvent medium for the reaction.

In addition to the advantage of extremely high yield of pure product obtained according to the method of the present invention, the method provides the further advantage of very rapid reaction so that the high yield is obtained more quickly than by known methods.

While the invention is not meant to be limited as to any specific theory as to how the reaction takes place and why the phosphorous oxychloride is so much more effective as a catalyst for this reaction, the following theory is given in the hopes that it will help others to further advance the art.

It is believed that the reaction actually takes place by the phosphorous oxychloride first reacting with the alcohol with the resulting phosphate-type reaction product further reacting with the benzoin to form the desired benzoin ether. While this mechanism of reaction has not been proved it is the mechanism that is believed to take place and could possibly explain the very high yields which are obtained according to the present invention.

The yields of the benzoin ethers according to the present invention average between 90 and 95% of the theoretical, which is substantially higher than the yields obtained by prior methods.

In addition to the advantages of higher yield and faster reaction, the present invention provides the further advantage of permitting the production of bisbenzoin ethers resulting from the reaction of an alkylene glycol with benzoin under the same conditions as set forth above. The bisbenzoin ethers of the present invention have many uses of considerable value. Thus, these bisbenzoin ethers are suitable for incorporation into curable molding and coating materials having bases of unsaturated resins. The bisbenzoin ethers can be used for producing clear finishes for resin products for wood boards, paper, plastics of all types, metal, cardboard, etc. In addition, they can be applied as coatings to protect the grain finish and decorative finish on various articles. Furthermore, the bisbenzoin ethers can be used in the graphic arts on photopolymers for printing plates to initiate ultraviolet curing of the plate, and the ethers can also be used in the electrical industry as conductors.

The bisbenzoin ethers of the present invention have the following structural formula:

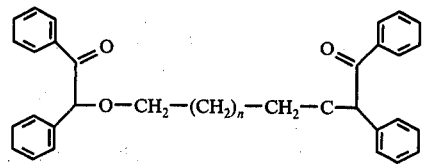

wherein $n = 0,1,2$.

The general method of preparing the benzoin ethers according to the present invention, including the bisbenzoin ethers, is as follows: the reaction flask is charged with the alcohol, benzoin and phosphorous oxychloride. As indicated above, an excess of the alcohol is used so that it can also act as the solvent for the reaction. Thus, for example, suitable proportions would be about 2.2 mols of the alcohol, about 0.25 mols of benzoin and about 0.95 mols of the phosphorous oxychloride. Hydrogen chloride gas is introduced into the reaction medium while heating under reflux for one hour. The reaction medium is cooled to room temperature, a small amount of water (e.g. 1 ml) is added and the medium is neutralized with NH$_4$OH. In the case of crystalline ethers the mixture is heated to 80° C and the ethers separated. Liquid ethers are separated at room temperature. Additional water (e.g. about 200 ml) is added, heated to 95° and the products separated. Solid ethers are recrystallized and liquid ethers are distilled.

The general advantages of the process of the present invention in addition to shorter reaction time and higher yield are less decomposition with the production of a cleaner crude product and the reactant acting as an efficient water scavenger for the reaction.

DESCRIPTION OF PREFERRED EMBODIMENTS

While the invention is not meant to be limited to any specific examples, the following examples are given to further illustrate the present invention.

EXAMPLE 1

53 g of benzoin is added to 71 g of methyl alcohol and 7.5 g of phosphorous oxychloride. The reaction solution is heated under refluxing while passing gaseous hydrogen chloride therethrough for a period of 30 minutes. The reaction mixture is cooled and neutralized with 200 ml of H₂O and NH₄OH to pH 7.0. An additional 200 ml of water is added, the reaction mixture heated to boiling and separated at 90°-95° C. The product is dried over a drying agent and filtered. The oil is distilled under high vacuum. The resulting benzoin-methyl ether boils at 121°-125° C/0.3-0.4 mm Hg. The yield is 92% of the theoretical.

By reacting the same amount of benzoin under the same conditions, however utilizing 105 g of trimethyl phosphate instead of the methyl alcohol and phosphorous oxychloride, the results obtained are substantially the same as above. This would appear to support the theory previously given as to the action of the phosphorous oxychloride in the reaction.

EXAMPLE 2

Example 1 above is repeated, however, using 101 g of ethyl alcohol. The yield of the resulting benzoin ethyl ether is about 93%, the resulting ether melting at 62°-63° C.

EXAMPLE 3

53 g of benzoin is added to 132 g of isopropyl alcohol followed by the addition of 7.6 g of phosphorous oxychloride. The solution is heated under reflux and hydrogen chloride gas is passed therethrough for 1 hour. This solution is cooled to room temperature and 200 ml of H₂O is added with NH₄OH to neutralize the mixture to pH 7.0. The mixture is heated to 80° C and water is removed. An additional 200 ml of H₂O is added and the mixture heated to boiling and separated. It is cooled, the isopropyl benzoin ether is collected and recrystallized as a solid. The melting point is 76°-78° C. The yield is 94%.

The same method is used to produce, in substantially the same yield, n-propyl benzoin ether, isobutyl benzoin ether, n-butyl benzoin ether, pentyl benzoin ether, cyclohexyl benzoin ether, etc.

EXAMPLE 4

This example illustrates the production of ethylene glycol benzoin ether (or bisbenzoin ether) according to this invention. 53 g of benzoin are added to 62 g of ethylene glycol to which is added 17 g of phosphorous oxychloride. The solution is heated under reflux and gassed with hydrogen chloride for 1 hour. The solution is cooled to room temperature and 200 ml of H₂O is added with NH₄OH to neutralize the mixture to pH 7.0. The mixture is heated to 80° C and the water is removed by separation. 200 ml of water is added and the mixture heated to boiling and separated. It is cooled, collected and recrystallized. The resulting ethylene glycol bisbenzoin ether has a melting point of 88°-90° C.

The same method may be used for the production of propylene glycol bisbenzoin ether as well as for the production of butylene glycol bisbenzoin ether.

While the invention has been illustrated in particular with respect to specific methods and products, it is apparent that variations and modifications thereof can be made.

What is claimed is:

1. Alkyl glycol bisbenzoin ethers of the formula:

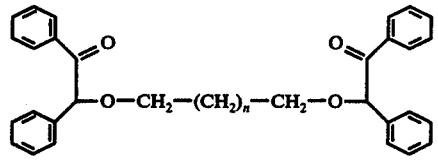

wherein $n$ equals 0, 1 or 2.

2. Alkyl glycol bisbenzoin ethers according to claim 1 wherein $n$ is 0.

3. Alkyl glycol bisbenzoin ether according to claim 1 wherein $n$ is 1.

4. Method of producing benzoin ethers, which comprises reacting an alkyl alchol with benzoin in the presence of phosphorous oxychloride and gaseous hydrogen chloride, the amount of said alcohol being in excess of the stoichiometric amount.

5. Alkyl glycol bisbenzoin ether according to claim 1 wherein $n$ is 2.

6. Method according to claim 4 wherein said reactin is effected under refluxing.

7. Method according to claim 4 wherein said alcohol is an alkylene glycol of up to 4 carbon atoms.

8. Method according to claim 4 wherein said alcohol is ethylene glycol.

* * * * *